United States Patent
Baumgold (10) Patent No.: US 10,908,090 B2
(45) Date of Patent: Feb. 2, 2021

(54) MICROARRAY SLIDES THAT ENHANCE FLUORESCENT SIGNALS VIA PLASMONIC INTERACTION

(71) Applicant: Chris Geddes, Baltimore, MD (US)

(72) Inventor: Jesse Baumgold, Bethesda, MD (US)

(73) Assignee: Chris Geddes, Baltimore, MD (US)

( * ) Notice: Subject to any disclaimer, the term of this patent is extended or adjusted under 35 U.S.C. 154(b) by 608 days.

(21) Appl. No.: 15/557,507

(22) PCT Filed: Mar. 7, 2016

(86) PCT No.: PCT/US2016/021140
§ 371 (c)(1),
(2) Date: Sep. 12, 2017

(87) PCT Pub. No.: WO2016/148951
PCT Pub. Date: Sep. 22, 2016

(65) Prior Publication Data
US 2018/0045644 A1      Feb. 15, 2018

Related U.S. Application Data

(60) Provisional application No. 62/217,989, filed on Sep. 14, 2015, provisional application No. 62/132,769, filed on Mar. 13, 2015.

(51) Int. Cl.
| | | |
|---|---|---|
| *G01N 21/64* | (2006.01) | |
| *G01N 33/543* | (2006.01) | |
| *G01N 33/553* | (2006.01) | |
| *G01N 21/552* | (2014.01) | |
| *G01N 21/77* | (2006.01) | |
| *G02B 21/34* | (2006.01) | |
| *B82Y 20/00* | (2011.01) | |

(52) U.S. Cl.
CPC ......... *G01N 21/648* (2013.01); *G01N 21/553* (2013.01); *G01N 21/554* (2013.01); *G01N 21/6428* (2013.01); *G01N 21/7703* (2013.01); *G01N 33/54373* (2013.01); *G01N 33/553* (2013.01); *G02B 21/34* (2013.01); *B82Y 20/00* (2013.01); *G01N 2021/6439* (2013.01); *G01N 2201/06113* (2013.01)

(58) Field of Classification Search
None
See application file for complete search history.

(56) References Cited

U.S. PATENT DOCUMENTS

| | | | | |
|---|---|---|---|---|
| 8,105,819 B2* | 1/2012 | Moore | ................. | G01N 33/551 435/287.1 |
| 10,571,465 B2* | 2/2020 | Szmacinski | .......... | G01N 21/648 |
| 2003/0107741 A1* | 6/2003 | Pyo | ....... | G01N 21/553 356/445 |
| 2004/0141300 A1 | 7/2004 | Takubo et al. | | |
| 2007/0166761 A1 | 7/2007 | Moore | | |
| 2011/0250402 A1* | 10/2011 | Oldham | ................. | G02B 5/008 428/172 |
| 2013/0115710 A1* | 5/2013 | Geddes | ................ | G01N 33/582 436/172 |
| 2014/0218738 A1* | 8/2014 | Bartoli | ............... | G01N 21/7703 356/450 |
| 2014/0256593 A1* | 9/2014 | Szmacinski | ...... | G01N 33/54373 506/9 |
| 2014/0287224 A1 | 9/2014 | Geddes | | |

FOREIGN PATENT DOCUMENTS

KR     20100002960 A     1/2010

OTHER PUBLICATIONS

Szmacinski ("Large Fluorescence Enhancements of Fluorophore Ensembles with Multilayer Plasmonic Substrates: Comparison of Theory and Experimental Results" Journal of Physical Chemistry C, vol. 116, No. 40, Oct. 11, 2012, pp. 21563-21571).*
International Search Report and Written Opinion dated Jun. 28, 2016 received in PCT/US2016/021140.
Lakowicz, J. et al., "Advances in Surface-Enhanced Fluorescence", J Fluoresc., vol. 14, No. 4, pp. 425-441, (2004).
Lakowicz, J. et al., "Plasmon-Controlled Fluorescence: A New Paradigm in Fluorescence Spectroscopy", Analyst, vol. 133, No. 10, pp. 1308-1346, doi:10.1039/b802918k, (2008).
Szmacinski, H. et al., "Fabrication and Characterization of Planar Plasmonic Substrates with High Fluorescence Enhancement", Journal of Physical Chemistry, vol. 114, No. 49, pp. 21142-21149, (2010).
Szmacinski, H. et al., "Large Fluorescence Enhancements of Fluorophore Ensembles with Multilayer Plasmonic Substrates: Comparison of Theory and Experimental Results", Journal of Physical Chemistry, vol. 116, No. 40, pp. 21563-21571, (2012).

(Continued)

*Primary Examiner* — Ann Y Lam
(74) *Attorney, Agent, or Firm* — Michele M. Wales; Inhouse Patent Counsel, LLC (57) ABSTRACT

The invention describes generating and use of a multi-layer plasmonic slide, wherein the plasmonic slide comprises at least 6 layers of metallic nanoparticles that can enhance the detection of fluorescent signals and wherein the plasmonic slide can be printed as a microarray of any size. The microarray containing the plasmonic slide can further be printed with a protein, a glycan, or an antibody. The multi-layer plasmonic slide is capable of detecting proteins, polynucleotides, and/or glycans at orders of magnitude lower concentration than non-plasmonic substrates.

26 Claims, 7 Drawing Sheets

(56) References Cited

OTHER PUBLICATIONS

International Preliminary Report on Patentability and Written Opinion dated Sep. 28, 2017 received in PCT/US2016/021140.
EPO Office Action dated Sep. 10, 2019 received in corresponding EP Application 16 710 598.0.
Office of Action dated Nov. 23, 2018 received in corresponding European Application, No. 16 710 598.0.
Response to the Correspondence from EPO dated Jun. 3, 2019 for application No. EP 16 71 0598.0-1020.

* cited by examiner

MICROARRAY SLIDES THAT ENHANCE FLUORESCENT SIGNALS VIA PLASMONIC INTERACTION

CROSS-REFERENCE TO RELATED APPLICATIONS

This application is a § 371 National Stage Application PCT/US16/21140 filed on Mar. 7, 2016, which claims priority to U.S. 62/132,769 filed on Mar. 13, 2015 and U.S. 62/217,989 filed on Sep. 14, 2015. These documents are hereby incorporated by reference in their entirety.

INTRODUCTION

Protein microarrays are typically analyzed using a biomolecule conjugated to a fluorescent probe. Although techniques for detecting proteins, polynucleotides, antibodies, peptides and glycans printed on microarrays are developed, these techniques are not able to amplify the resulting signals efficiently.

It is known that plasmonic surfaces can enhance fluorescence intensity from fluorophores proximal to a layer of metal nanoparticles. The physical basis for this effect, also referred to as Metal Enhanced Fluorescence (MEF) [1], is well described and has been extensively reviewed [2-5]. It is generally accepted that MEF is caused by the non-radiative coupling of the fluorophore dipole with the electron cloud of the metal (i.e. surface plasmons), thereby altering the fluorescence characteristics. Specifically, the plasmonic effect causes fluorescence intensity of the fluorophore to increase substantially and fluorescence lifetime of the fluorophore to decrease, resulting in an increased photostability [1,2]. In general, MEF is a near-field effect, occurring when a fluorophore is within 5-50 nm of a metal (e.g., nanoparticle), which supports surface plasmons [5].

Gold plasmonic surfaces have been used as substrates for protein microarrays and these surfaces have been shown to enhance fluorescence. However maximal enhancement on a gold plasmonic surface occurs in the near-infra-red, thus requiring fluorescent dyes and microarray readers capable of fluorescing and reading in the near-infra-red. Such dyes and readers are not widely available and for this reason plasmonic surfaces have not been used for microarrays.

Thus, there is a need to develop better microarray substrates that can amplify fluorescent signals improving the detection of proteins, glycans, polynucleotides or antibodies at orders of magnitude lower concentration than substrates currently in use.

SUMMARY OF THE INVENTION

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject.

The present invention relates to a multi-layer plasmonic slide comprising an adherence layer (layer 1), a silver mirror layer (layer 2), an adherence layer (layer 3), a dielectric layer (layer 4), a thin silver layer (layer 5), and a stabilization layer (layer 6). The invention further comprises coating titanium dioxide ($TiO_2$) in layer 1, silver (Ag) in layer 2, titanium dioxide ($TiO_2$) in layer 3, silicon dioxide ($SiO_2$) in layer 4, silver (Ag) in layer 5, and silicon dioxide ($SiO_2$) in layer 6.

As we describe herein, the multi-layer plasmonic slide comprises a silver surface with optimal enhancement in the visible region, thereby enabling use of dyes with absorption and emission maxima in the visible region, along with the use of widely available slide readers capable of reading such dyes. Moreover, because silver plasmonic surfaces can be quite delicate, we hardened the plasmonic surface by coating it with a thin layer of SiO2.

In a preferred embodiment, layer 2 is positioned on layer 1, layer 3 is positioned on layer 2, layer 4 is positioned on layer 3, layer 5 is positioned on layer 4, and layer 6 is positioned on layer 5.

In preferred embodiments, the thickness of each layer of the plasmonic slide is as following: (a) layer 1 is about 35-45 nm (preferably about 40 nm), and/or is deposited at about 2-5 angstroms per second (preferably at about 3 angstroms per second); (b) layer 2 is about 180-220 nm (preferably about 200 nm), and/or is deposited at about 3-6 angstroms per second (preferably at about 4 angstroms per second); (c) layer 3 is about 5-7 nm (preferably about 6 nm), and/or is deposited at about 0.5-1.5 angstroms per second (preferably at about 1 angstrom per second); (d) layer 4 is about 35-45 nm (preferably about 40 nm), and/or is deposited at about 0.5-1.5 angstroms per second (preferably at about 1 angstrom per second); (e) layer 5 is about 11-15 nm (preferably about 13 nm), and/or is deposited at about 0.1-1 angstroms per second (preferably at about 0.5 angstroms per second); and/or (f) level 6 is about 18-22 nm (preferably about 20 nm), and/or is deposited at about 0.5-1.5 angstroms per second (preferably at about 1 angstroms per second).

In preferred embodiments, the plasmonic slide described herein comprises about 40 nm of titanium dioxide ($TiO_2$), about 200 nm of silver (Ag), about 6 nm of titanium dioxide ($TiO_2$), about 40 nm of silicon dioxide ($SiO_2$), about 13 nm of silver (Ag), and about 20 nm of silicon dioxide ($SiO_2$). In even further preferred embodiments, the plasmonic slide described herein comprises about 40 nm of titanium dioxide ($TiO_2$) deposited at about 3 angstroms per second, about 200 nm of silver (Ag) deposited at about 4 angstroms per second, about 6 nm of titanium dioxide ($TiO_2$) deposited at about 1 angstrom per second, about 40 nm of silicon dioxide ($SiO_2$) deposited at 1 angstrom per second, about 13 nm of silver (Ag) deposited at about 0.5 angstroms per second, and about 20 nm of silicon dioxide ($SiO_2$) deposited at about 1 angstrom per second. In further preferred embodiments, the slide is plasma-cleaned. Additional embodiments include the coating of each layer of the slide by using magnetron sputtering.

In preferred embodiments, the slide is vacuum-annealed at about 150° C. to about 250° C., preferably at about 200° C. In further preferred embodiments, the slide is further coated with epoxy silane and is printed as a microarray in any size. In yet preferred embodiments, the slide is printed at about 250-350 pL per spot, preferably at about 300 pL, and the resulting spot is about 150-250 µm in diameter, preferably at about 200 µm in diameter.

As described herein, the microarray is printed with a protein, a glycan, or an antibody. In further embodiments, the protein, glycan, or antibody is included in at least three spots on the microarray.

In preferred embodiments, the invention presents a method of detecting a concentration of a protein, a glycan, or an antibody. This method can comprise contacting a protein, a glycan, or an antibody with the multi-layer plasmonic slide and then tagging a Cy5 fluorescent probe or a Cy3 fluorescent probe on a protein, a glycan, or an antibody. Additionally, a microarray laser scanner is used to detect a protein, a glycan, or an antibody and the intensity of fluorescent signals are measured at about 532 nm for Cy3 and at 635 nm for Cy5.

In preferred embodiments, the protein described herein is biotinylated-BSA, mouse IgG, or human IgG wherein the concentration of the protein printed on the array is between 0.1 ng/ml and 0.1 mg/ml. In further preferred embodiments, the human IgG is detected with biotinylated anti-human IgG followed by streptavidin-Cy3 or streptavidin-Cy5. In another preferred embodiment, the mouse IgG is detected with biotinylated anti-mouse IgG followed by streptavidin-Cy3 or streptavidin-Cy5. In yet another preferred embodiment, the biotinylated-BSA is detected with either streptavidin-Cy3 or streptavidin-Cy5.

In preferred embodiments, the biotinylated-BSA can be detected at least 1-2, 2-3, 3-4, or 4-5 orders of magnitude lower concentrations using Cy5 fluorescent probe whereas the biotinylated-BSA is saturated at concentration of 0.01, 0.02, 0.03, 0.04, 0.05, 0.06, 0.07, 0.08, 0.09, or 0.1 mg/mL with streptavidin-Cy3.

In preferred embodiments, the glycan is detected with a biotinylated-glycan binding protein followed by binding with either streptavidin-Cy3 or streptavidin-Cy5. In further preferred embodiments, at least 5 different glycans including but limiting to 4-aminobutyl β-D-galactopyranoside, aminoethyl β-D-galactopyranoside, glycyl-lactose, α-GalNAc-Serine, and Galβ1-3GalNAcα1-serine (T antigen) are detected at least two orders of magnitude lower concentrations using Cy5 fluorescent probe. In further preferred embodiments, the detection of a protein, a glycan, or an antibody with Cy5 fluorescent probe yields brighter spots on the microarray than Cy3 fluorescent probe.

In preferred embodiments, the present invention also introduces a method of making the multi-layer plasmonic slide comprising steps of: (a) preparing a plasma-clean borosilicate glass slide, (b) coating layer 1 of the said slide with titanium dioxide ($TiO_2$) by magnetron sputtering, (c) Coating layer 2 of the said slide with silver (Ag) by magnetron sputtering, (d) Coating layer 3 of the said slide with titanium dioxide (TiO2), (e) coating layer 4 of the said slide with silicon dioxide ($SiO_2$), (f) coating layer 5 of the said slide with silver (Ag), (g) coating layer 6 of the said slide with silicon dioxide ($SiO_2$), (h) coating the slide with epoxy silane using a dipping process, and (i) drying the slide under nitrogen and vacuum-annealing at about 150° C. to about 250° C.

BRIEF DESCRIPTION OF DRAWINGS

FIG. 1 shows the comparison of the plasmonic slides and Corning epoxy-coated slides on proteins. Slides are printed with replicate 9×8 arrays of protein. In each array, the first 3 spots are biotinylated-BSA (Bt-BSA) at 0.1 mg/mL for the top row and decreasing by order of magnitude to 0.1 ng/mL in the $8^{th}$ row. The middle 3 spots are mouse IgG (mIgG) starting at 0.1 mg/mL in the top row and decreasing to 0.1 ng/mL in the $8^{th}$ row. The right-hand 3 spots are human IgG (hIgG0 starting at 0.1 mg/mL in the top row and decreasing to 0.1 ng/mL in the $8^{th}$ row. The first 3 spots in the $9^{th}$ row are a negative control (printing buffer); the next 3 spots in the $9^{th}$ row are a positive control (Cy3 labeled anti-goat IgG at 0.01 mg/mL. Each array is probed with either streptavidin-Cy3 (SA-Cy3), streptavidin-Cy5 (SA-Cy5) or biotinylated anti-mouse IgG (1 ug/mL) followed by SA-Cy3 or SA-Cy5 at 0.5 ug/mL, or with biotinylated anti-human IgG (1 ug/mL) followed by SA-Cy3 or SA-Cy5 at 0.5 ug/mL. Slides are then read in a slide reader.

FIG. 2 shows the comparison of the plasmonic slides and Corning epoxy-coated slides on glycans. Slides are printed with replicate 6×6 arrays of glycans. In each array, the first 3 spots of row 1 are 4-aminobutyl β-D-galactopyranoside at 100 uM followed by 3 spots of this glycan at 10 uM. The first 3 spots in row 2 are aminoethyl β-D-galactopyranoside at 100 uM, followed by 3 spots of this glycan at 10 uM. In row 3, the first 3 spots are 100 uM of glycyl-lactose, followed by 3 spots of glycyl-lactose at 10 uM. In row 4, the first 3 spots are 100 uM of α-GalNAc-Serine followed by 3 spots of 10 uM of this. In row 5, the first 3 spots are Galβ1-3GalNAcα1-serine (T antigen) at 100 uM, followed by 3 spots of this at 10 uM. The first 3 spots in row 6 are a negative control followed by 3 spots of a positive control. Each of these arrays was assayed using either biotinylated-HPA at 10 ug/mL, PNA-biotin at 10 ug/mL or RCA-1-Biotin at 1 ug/mL followed by SA-Cy3 or SA-Cy5 at 0.5 ug/mL as indicated in the figure.

FIG. 3 shows the quantitation of protein microarray. The red lines are from the plasmonic slides and the black lines are from Corning slides. Each data point represents mean+/−S.D. from triplicate spots.

FIG. 4 shows the quantitation of glycan microarrays. The indicated glycan is printed in triplicate at either 10 or 100 uM, then detected with biotinylated-PNA (1 ug/mL) or biotinylated-RCA-1 (1 ug/mL). Streptavidin-Cy3 or -Cy5 are used at 0.5 ug/mL. Data represent mean+/−S.D. from triplicate spots.

DETAILED DESCRIPTION

The details of one or more embodiments of the invention are set forth in the accompanying drawings and the description below. Other features, objects, and advantages of the invention will be apparent from the description and drawings, and from the claims.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

We describe herein a new method that enhances fluorescent detection of proteins (including antibodies), polynucleotides, and/or glycans spotted on protein or glycan microarrays by coating microarray slides with a layer of plasmonic nanoparticles. The plasmonic slides in present invention are multilayered glass slides comprising a coating with a thin layer of metal nanoparticle then with epoxy silane. The new platform further incorporates the properties of plasmonic effect to strengthen fluorescent signals from dyes that bind to protein or glycan microarrays. The epoxy silane further promotes strong adherence of proteins, polynucleotides, and glycans and can be used to spot biomolecules just like conventional slides.

Fluorescent molecules are commonly applied in the field of biomedical sciences to detect biological matters. Protein microarray, for example, is a high-throughput assay to detect multiple activities of proteins in parallel. The general mechanism is to add specific probe molecules labeled with fluorescent dyes to the array which comprises a support surface of glass slide and substances such as nitrocellulose membrane and microtitre plates that can capture and immobilize proteins. Upon adding a biological sample, for instance, the fluorescent labeled probe then can react with the immobilized proteins and thus emit fluorescent signals that are read by laser scanners. However, one of the major limitations of this application is the lack of brightness when ultrasensitive detection (e.g. low protein concentrations) is required. Thus, enhancing fluorescence detection power is essential to overcome this common constraint.

Metallic nanoparticles such as silver exhibit attractive properties in light manipulation and demonstrate highly efficient interactions with visible light and near infrared (NIR), resulting from the excitation of localized surface plasmon resonance (LSPR). The use of metal nanoparticles, the plasmonic layer on the slide, to amplify fluorescent molecules has been studied by several research groups (Szmacinski et al., J Phys Chem C Nanometer Interfaces. 2012 Oct. 11; 116(40): 21563-21571; Lakowicz et al., Analyst. 2008 October; 133(10): 1308-1346). In principal, the plasmonic effect, resulting in light trapping, involves the coupling of excitation light into an LSPR-fluorophore system (near-field) and decoupling of fluorescence emission for effective detection in the far-field. Additionally, a layer of mirrors can also be added underneath the metallic nanostructures in order to increase the excitation and emission efficiency.

As described herein, the present invention involves constructing a multi-layer plasmonic slide which comprises at least 6 layers in the order of: an adherence layer (preferably made with titanium dioxide), a silver mirror layer, another adherence layer (preferably also made with titanium dioxide), a dielectric layer (preferably made with silicone dioxide), a thin silver layer, and another dielectric layer (preferably made with silicone dioxide). This newly invented plasmonic slide can surprisingly maximize the overall intensity of fluorescent signals, especially for the signals that otherwise are difficult to be detected by using conventional, non-plasmonic technologies. In a preferred embodiment, the invention comprises adding laer 6, comprising an additional stability layer, and layer 7, comprising an additional adherence layer, to increase overall adherence and stability. The multi-layer slides described herein can be used as a substrate of the microarray, allowing for the accurate detection of extremely small quantities of proteins, polynucleotides, or glycans that was not possible before.

To demonstrate the superior fluorescent detection capabilities of the invented plasmonic slide, we first construct a microarray consisting of the plasmonic slides and then compare it to a counterpart consisting of non-plasmonic commercially available epoxy slides. As a result, the plasmonic slide of the present invention can detect 10-100 fold lower concentrations of proteins than the non-plasmonic slide. Additionally, microarrays consisting of plasmonic slides described herein are capable of detecting glycans at 100-10,000 fold lower concentrations than the non-plasmonic slides. Therefore, the present invention is particularly useful for detecting low concentrations of proteins (including antibodies), polynucleotides, and/or glycans and potentially is a robust tool to apply in the fields of medical diagnostics and therapeutics.

Definitions:

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) $4^{th}$ ed., John Wiley & Sons, Inc.), which are incorporated herein by reference.

As used herein, "plasmonic effect" is defined as the effect that is caused by the non-radiative coupling of the fluorophore dipole with surface plasmons, thereby altering the fluorescence characteristics. Surface plasmons are those plasmons that are confined to silver surfaces.

As used herein, "protein" is defined as macromolecules comprising of one or more long chains of amino acid residues and may exert biological functions. In present invention, protein refers to any kind of existing proteins, including antibodies.

As used herein, "antibody" is defined as immunoglobulin molecules and immunologically active portions of immunoglobulin molecules produced by B cells that is used by the immune system to bind to and neutralize foreign substances, also called "antigen", from sources such as viruses and bacteria. Examples of the term "antibody" include, but not limited to: single chain Fvs (scFvs), Fab fragments, Fab' fragments, F(ab')2, disulfide linked Fvs (sdFvs), Fvs, and fragments comprising or alternatively consisting of, either a VL or a VH domain. Any antibody targeting any of the antigens can be used in the present invention.

As used herein, a "polynucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term polynucleotide, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

As used herein, "glycan" refers to compounds comprising a large number of monosacchatides linked glycosidically. Glycan is essentially saccharides that can be attached to a wide variety of biological molecules through an enzyme process called glycosylation. Additionally, glycan can also be referred to the carbohydrate portion of a glycoconjugate, such as a glycoprotein, glycolipid, or a proteoglycan. N-linked glycans, O-linked glycans, and glycosaminoglycans are the three major types of glycans.

As used herein, "magnetron sputtering" is defined as a form of Physical Vapor Deposition (PVD) coating technology. PVD describes a variety of vacuum deposition methods used to deposit thin films by the condensation of a vaporized form of the desired film material onto various workpiece surfaces. In addition, magnetron sputtering is a plasma coating process whereby sputtering material is ejected due to bombardment of ions to the target surface. The vacuum chamber of the PVD coating machine is filled with an inert gas, such as argon. By applying a high voltage, a glow discharge is created, resulting in acceleration of ions to the target surface and a plasma coating. The argon-ions will eject sputtering materials from the target surface (sputtering), resulting in a sputtered coating layer (e.g the plasmonic layer containing silver) on the slide.

As used herein, "deposited at about x angstroms per second" refers to the rate at which a thin film is deposited onto a target surface. This rate can be controlled by altering the temperature and high voltage in the sputtering system.

As used herein, "vacuum-annealed" occurs after completing the deposition of all layers, the slides are then heated while still under vacuum of the magnetron sputtering system to 180 degrees to 220 degrees for the indicated time.

As used herein, "plasma cleaned involves the removal of impurities and contaminants from surfaces through the use of an energetic plasma or Dielectric barrier discharge (DBD) plasma created from gaseous species. Gases such as argon and oxygen, as well as mixtures such as air and hydrogen/nitrogen are used.

As used herein, "epoxy silane", refers to when the silane is functional at both ends and one end is an active chemical group such as amino (NH2), mercapto(SH) or isocyanato (NCO) or epoxy. This functionality can react with functional groups in an industrial resin or bio molecule such as peptides, oligonucleotides or DNA fragments. The other end often consists of a halo (chloro most often) or alkoxy (most often methoxy or ethoxy) silane. This functionality is converted to active groups on hydrolysis called silanols. The silanols can further react with themselves, generating oligomeric variations. All silanol variations can react with active surfaces that themselves contain hydroxyl (OH) groups such as glass.

As used herein, "printed" or "printed on a slide" refers to either contact or non-contact printing of very small volumes (typically less than 10 micro-liters) onto a well-defined position on the slide, resulting in a small spot typically less than 400 microns in diameter.

As used herein, a protein or glycan can be labeled with a detectable markers, which include, but are not limited to, radioactive isotopes, affinity labels, fluorophores, biotin, enzymes (e.g., alkaline phosphatase), enzyme substrates, ligands and antibodies, etc. See Jablonski et al., NUCLEIC ACIDS RES. (1986) 14:6115-6128; Nguyen et al., BIOTECHNIQUES (1992) 13:116-123; Rigby et al., J. MOL. BIOL. (1977) 113:237-251. Indeed, the protein or glycan may be modified in any conventional manner for various molecular biological applications. Techniques for label proteins, polynucleotides, and/or glycans are conventional in the art.

As used herein, "fluorescence" is defined as the emission of light by a substance that has absorbed light or other electromagnetic radiation.

As described herein, "microarray" refers to an array of spotted proteins, arranged in either rows or columns, of glycans, antibodies, polynucleotides, or other bio molecule printed onto a planar surface and capable of binding a target molecule. One example of a micro array is a protein microarray (or protein chip) which is a high-throughput method to detect the interactions, activities, and functions of proteins. Three major types of protein microarrays include analytical microarray (also known as capture array), functional protein microarray, and reverse phase protein microarray.

In the present disclosure, "a biological sample" is defined broadly and includes any biospecimen taken from a patient. The biological sample can include, for example, peripheral blood, stool, urine and/or bone marrow sample, and/or tissue from a surgical resection. In a preferred embodiment, the biological sample is a peripheral blood sample.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

The term "patient" or "subject" as used herein in reference to individuals where their biological sample is being tested using the plasmonic slides described herin. Examples of such individuals can encompass veterinary uses, such as, for example, the testing of a rodent (e.g. a guinea pig, a hamster, a rat, a mouse), rabbit, murine (e.g. a mouse), canine (e.g. a dog), feline (e.g. a cat), equine (e.g. a horse), bovine (e.g., cow) a primate, simian (e.g. a monkey or ape), a monkey (e.g. marmoset, baboon), an ape (e.g. gorilla, chimpanzee, orangutan, gibbon). In preferred embodiments the mammal is a human.

Other aspects and embodiments of the invention provide the aspects and embodiments described above with the term "comprising" replaced by the term "consisting of" and the aspects and embodiments described above with the term "comprising" replaced by the term "consisting essentially of".

As used herein, "and/or" is to be taken as specific disclosure of each of the two specified features or components with or without the other. For example "A and/or B" is to be taken as specific disclosure of each (i) A, (ii) B and (iii) A and B, just as if each is set out individually.

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Construction of the Multi-Layer Plasmonic Slides and Microarray

A multi-layer plasmonic slide can be manufactured by using magnetron sputtering to coat a series of nanoparticle layers. In the present invention, at least 6 layers are coated on each plasmonic slide. For layer 1, the first adherence layer, about 35-45 nm, preferably 40 nm of titanium dioxide ($TiO_2$), is deposited at about 2-5 angstroms per second, preferably at about 3 angstroms per second. For layer 2, a silver mirror layer, around 180-220 nm, preferably 200 nm of silver (Ag), is deposited at about 3-6 angstroms per second, preferably 4 angstroms per second. For layer 3, a second adherence layer, about 5-7 nm, preferably about 6 nm of titanium dioxide ($TiO_2$), is deposited at about 0.5-1.5 angstroms per second, preferably at about 1.0 angstrom per second. For layer 4, a dielectric layer, about 35-45 nm, preferably 40 nm of silicone dioxide ($SiO_2$), is deposited at about 0.5-1.5 angstroms per second, preferably 1.0 angstrom per second. For layer 5, a second silver layer, about 11-15 nm, preferably about 13 nm of silver (Ag), is deposited at about 0.1-1 angstroms per second, preferably about 0.5 angstroms per second. For layer 6, another dielectric layer, about 18-22 nm, preferably 20 nm of silicone dioxide ($SiO_2$), is deposited at around 0.5-1.5 angstroms per second, preferably 1.0 angstrom per second. Additionally, the positions of the nanolayers from top to bottom on the plasmonic slide follow as: layer 1, layer 2, layer 3, layer 4, layer 5, and layer 6.

Upon the completion of metal coatings, the plasmonic slides are then vacuum-annealed to prevent any detectable surface contamination or oxidation and add epoxy silane in order to allow strong adherence of proteins, glycans, polynucleotides or antibodies.

Additionally, the prepared multi-layer plasmonic slides can be printed as a microarray in any size. The construction of the microarray can be achieved by using protocols that are well described in the art. The substitution of the conventional glass surface on the microarray with the present proprietary plasmonic slide is expected to yield enhanced fluorescent signals. In preferred embodiments, the slide is printed at around 250-350 pL per spot, preferably 300 pL per spot which then results in about 150-250 μm in diameter, preferably about 200 μm in diameter. Similar to the method used in the conventional microarray, the microarray printed with multi-layer plasmonic slides can then further printed with any proteins, glycans, polynucleotides, or antibodies of interest. In preferred embodiments, at least 3 spots on each microarray.

Comparison of the Protein Detection by Array Containing Plasmonic Slides and By the Conventional Array As previously described, protein microarray is a standard, high-throughput method for detecting the activities and functions of proteins on a large scale. The microarray normally contains a support surface such as glass slide to which the proteins is bound. Probe molecules, typically labeled with a fluorescent dye, are also added. The reaction between the probe and the protein emits a fluorescent signal. However, technical challenges often occur especially while handling proteins with low abundance.

As described herein, the new plasmonic nanolayer on the array yields stronger signal level that improves the quality of the output.

In order to determine the fluorescence enhancement offered by the plasmonic effect on the plasmonic slides, epoxy silane-coated multi-layer plasmonic slides with conventional epoxy silane-coated slides are compared. Three different proteins (biotinylated-BSA, mouse IgG and human IgG) are spotted on each slide in triplicate at concentrations starting at 0.1 mg/mL and decreasing by order of magnitude down to 0.1 ng/mL. In addition, each protein is tagged with either a Cy5 fluorescent probes or a Cy3 fluorescent probe and the concentrations of the proteins are detected with a microarray laser scanner. The Cy5 signals are measured at about 635 nm and the Cy3 signals are measured at around 532 nm. In a further preferred embodiment, any protein can be employed on the plasmonic slides.

Figure 3:
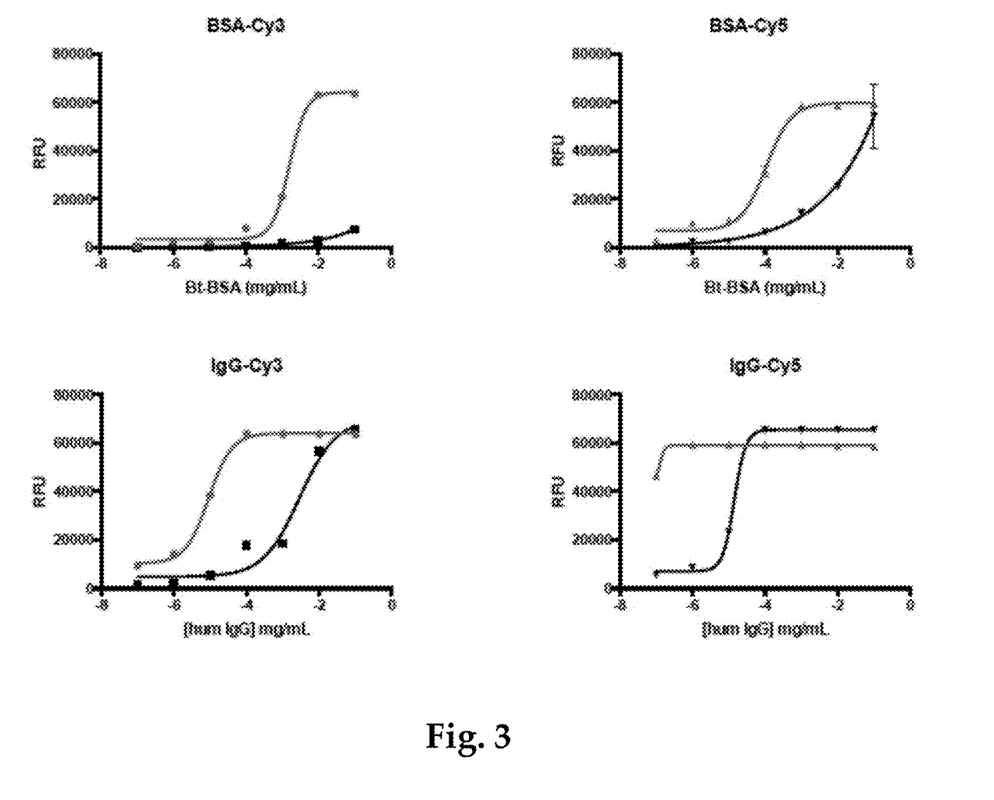

In preferred embodiments, the Cy3 signal from the plasmonic slides is below 10,000 RFU at concentrations of Bt-BSA under $10^{-4}$ mg/mL then increases rapidly to 63,000 RFU as the concentration is raised to $10^{-1}$ mg/mL (see red line FIG. 3, top left panel) In contrast, remains under 10,000 RFU throughout the entire concentration range (black line, FIG. 3, top left). Similarly, with Cy5 fluorescent probe detection, the top 3 concentrations are saturated in plasmonic slides whereas with the Corning slides, the top concentration is just barely saturated (FIG. 3, top right).

Figure 1:
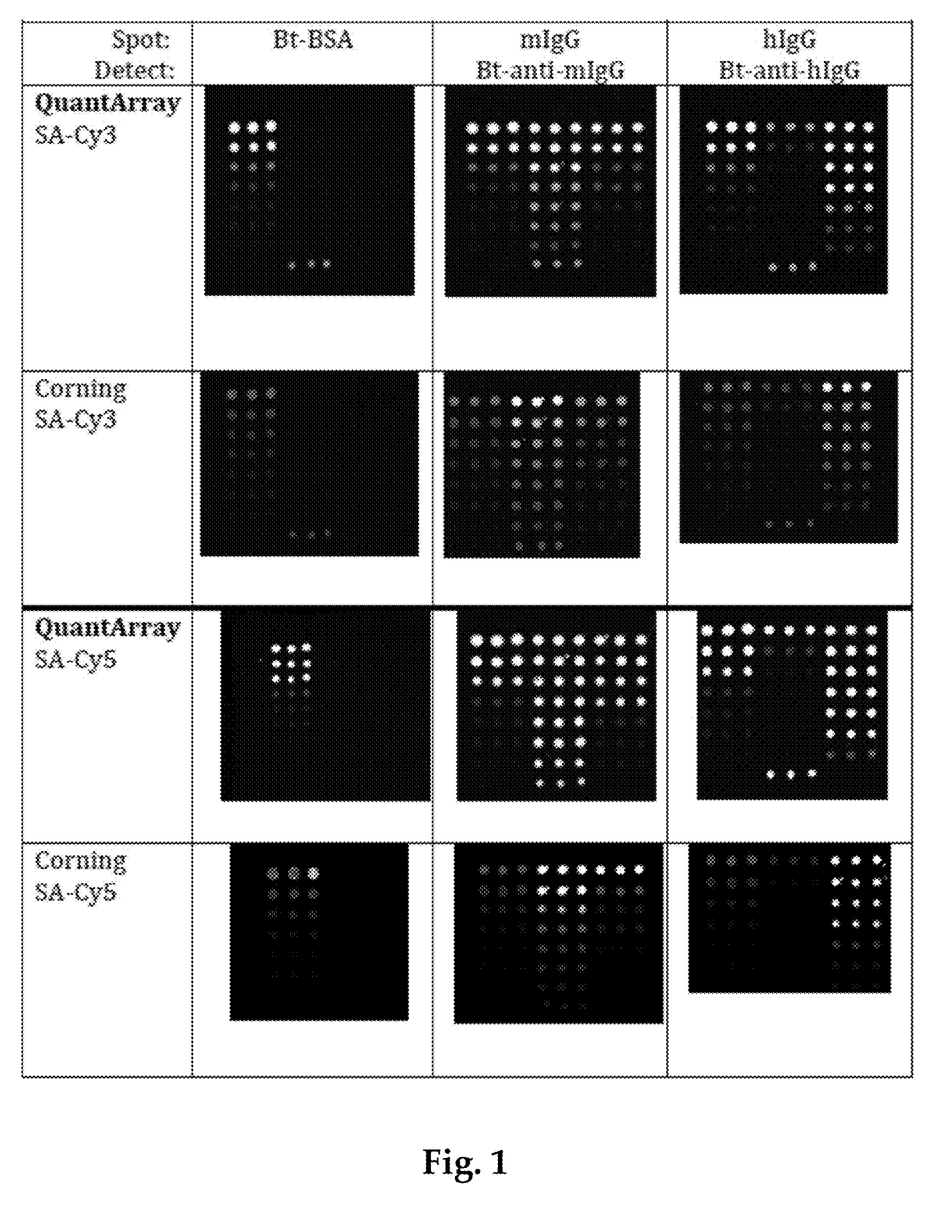

In preferred embodiments, a similar pattern is observed with both the mouse IgG and the human IgG, with the plasmonic slides having significantly stronger signals than the Corning slides. As shown in FIG. 3, bottom left, the curve obtained from increasing the concentration of human IgG increased from 9,324 RFU at $10^{-7}$ mg/mL (red line) to a saturating value of around 63,000 RFU at $10^{-4}$ mg/mL whereas with the Corning slides, the signal was only 17,000 RFU at $10^{-4}$ mg/mL (black line in FIG. 3, bottom left). In further preferred embodiments, and as shown in FIG. 1, the anti-mouse IgG used in these studies cross-reacted with human IgG resulting in a strong signal for human IgG. In all cases, Cy5 detection result in signals that are stronger than with Cy3 detection. This phenomenon is consistent with the wavelength-dependence of the plasmonic effect.

In other preferred embodiments, multi-layer plasmonic slides result in spots that are considerably brighter than spots on non-plasmonic slides, and are capable of detecting at least 1-2, 2-3, 3-4, or 4-5 orders of magnitude lower concentrations of protein compared to non-plasmonic conventional slides using the longer wavelength Cy5 fluorescent probe. Additionally, when using the Cy3 shorter wavelength dye, the fluorescence enhancement is not as pronounced, although still clear. Thus, these plasmonic slides will be useful for detecting low concentrations of proteins or antibodies.

Comparison of the Glycan Detection by Array Containing the Plasmonic Slides and by the Conventional Array Analysis of glycans on microarrays is an emerging and exciting area and the technology is well known by the skilled artisan. Investigations of carbohydrate-protein interactions have been revolutionized by the availability of glycan microarrays comprised of hundreds of defines glycan structures.

In order to demonstrate the utility of the multi-layer plasmonic slides for glycan microarray, we evaluate the ability of these slides to enhance the fluorescence from 1, 2, 3, 4, 5, 6, 7, 8, 9, or 10 glycans as detected by their respective biotinylated-glycan binding proteins and streptavidin labeled Cy3 or Cy5.

Figure 4:
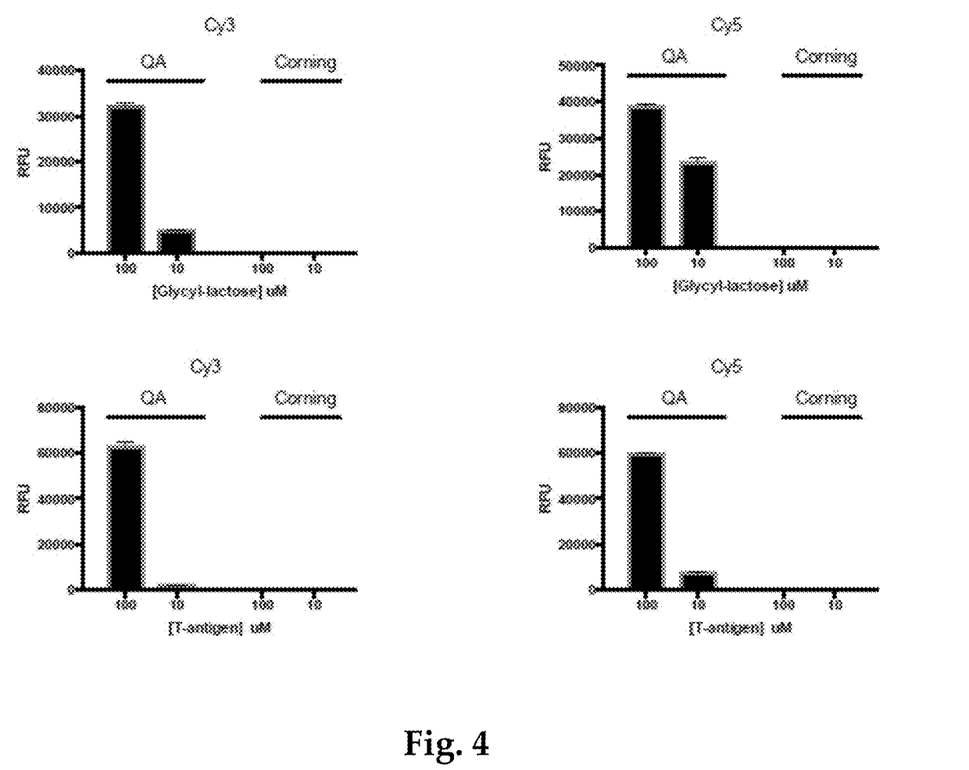
Figure 5:
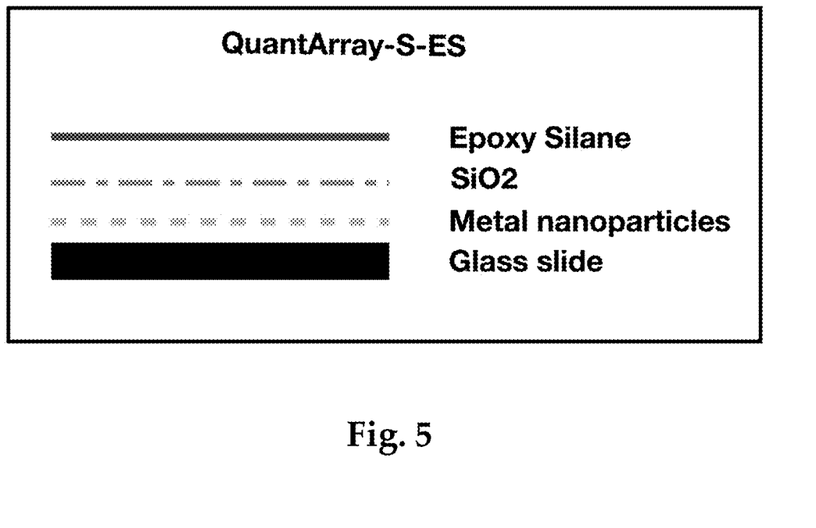
FIG. 5 is a schematic representation of QuantArray-S-ES slides.
Figure 6:
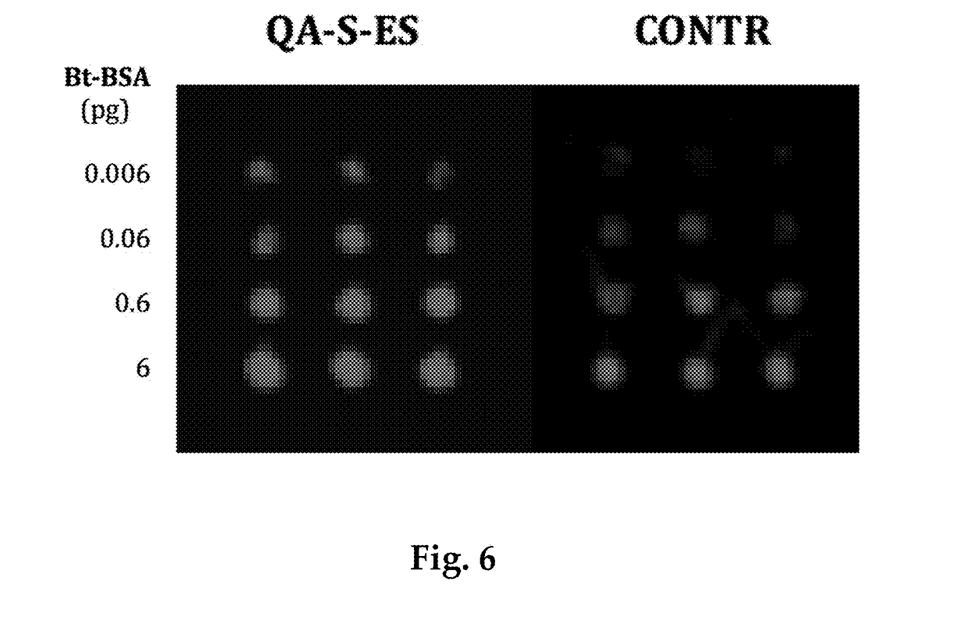
FIG. 6 shows a comparison of QuantArray-S-ES slides with control slides. In this example, control slides are borosilicate glass slides spotted with biotinylated protein. Both types of slides were treated with epoxy silane. QuantArray-S-ES slides were shown to detect spots of 0.006 pg of biotinylated (Bt)-BSA, whereas the control slides were barely able to detect 0.06 pg of Bt-BSA. Accordingly, an approximately 30-fold increase in sensitivity due to plasmonic metal nanoparticles was observed.
Figure 7:
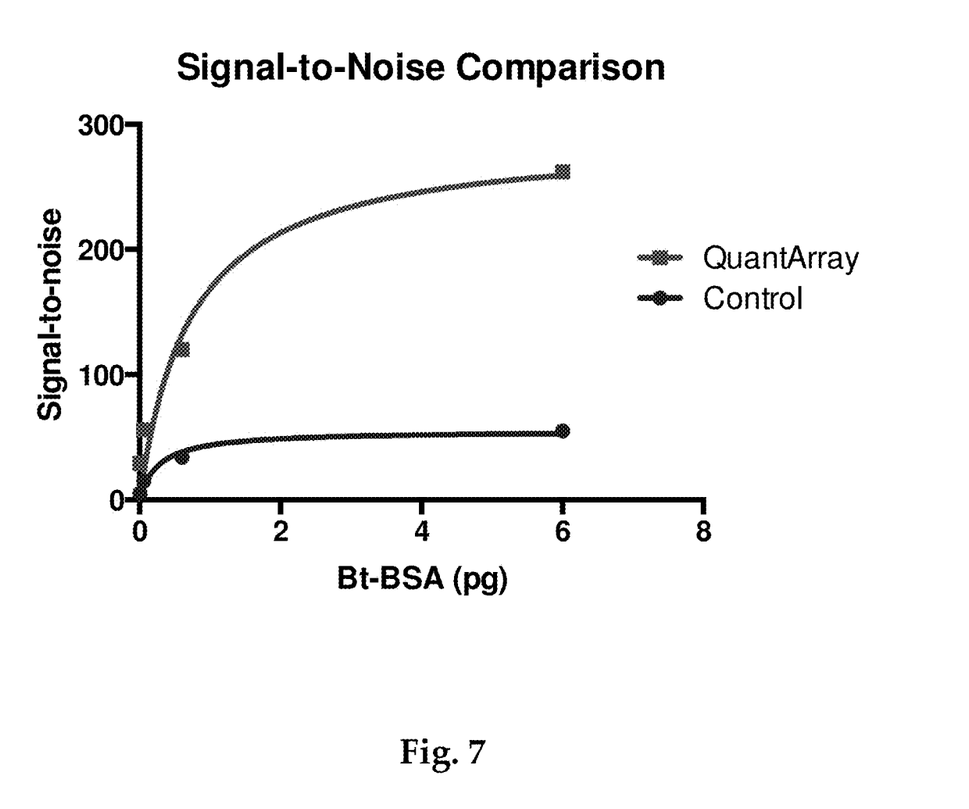
FIG. 7 shows a comparison of the signal-to-noise at various different Bt-BSA concentrations. The background in the QuantArray-S-ES slides was approximately twice that of the control slides. At 6 pg of Bt-BSA, the signal-to-noise of the QuantArray-S-ES slides was 4.8 fold higher than that of the control slides.

1, 2, 3, 4, 5, 6, 7, 8, 9, or 10 glycans including but not limiting to 4-aminobutyl β-D-galactopyranoside, aminoethyl β-D-galactopyranoside, glycyl-lactose, α-GalNAc-Serine, and Galβ1-3GalNAcα1-serine (T antigen) are spotted in triplicates, then incubated each sub-array in its respective biotinylated glycan binding protein. In other preferred embodiments, with the Cy3 probes, the glycyl-lactose (100 μM) spots as detected with Bt-HPA are considerably brighter on the plasmonic slides than on the Corning slides. In fact, as shown in FIG. 4, the glycyl-lactose (100 uM) spot had a relative fluorescent reading of 31,878 RFU on the QuantArray slide, but only 19 RFU on the Corning slide. Similarly at 10 uM, the glycyl-lactose spots had a reading of 4,650 RFU on the QuantArray slide, but only 31 on the Corning slide. In other words, the QuantArray slides were able to detect glycyl-lactose at 100 and at 10 uM whereas the Coring slides were not able to detect this glycan. A similar observation was made when using Cy5 probe (see FIG. 4 top right). Similarly, the T-antigen was easily detectable on QuantArray slides at 100 and at 10 uM with 62,618 and 1,911 RFU respectively, wherease these glycans were not detectable on Corning slides (see FIG. 4 bottom).

In preferred embodiment, glycyl-lactose at any concentration between 10 μM and 100 μM is detected with Bt-RCA-I binding protein followed by streptavidin-Cy3 or Cy5. In further preferred embodiments, this glycan results in very bright spots on the plasmonic slides but is not even detectable on the Corning slides. As shown previously, detection with Cy5 probe results in spots that are brighter than with the Cy3 probe.

In other preferred embodiments, Galβ1-3GalNAcα1-serine, the T antigen, is spotted at any concentration between 10 μM and 100 μM. At 100 μM, this glycan yielded very bright spots with both probes and at 10 μM, significant spot with Cy5 is also observed. In addition, we compared the inter-slide variation in plasmonic slides (data not shown) and found that both Cy3 and Cy5 probes has excellent reproducibility. Thus, similar to the findings reported in the protein assay, the glycans can also be detected at least 2-3 orders of magnitude lower concentrations using Cy5 fluorescent probes.

Other preferred probes/dyes/labels that can be used to detect proteins, polynucleotides, and glycans include any of the Alexa dyes, any of the DyLight dyes, any of the CF Dyes, etc, all of which are well known to the skilled artisan. Similarly, the proteins, polynucleotides, and glycans can be detected using antibodies or other labels known in the art.

QuantArray slides (also referred to herein as QuantArray-S-ES slides) are useful in microarray studies that need additional sensitivity. QuantArray-S-ES slides were shown to detect approximately 30-fold lower protein concentrations than control slides with a similar surface chemistry. Additionally, the signal-to-noise of the QuantArray slides was shown to be 4.8 fold higher than the control slides.

EXAMPLES

Example 1

Preparation of Plasmonic Slides

To make multi-layer plasmonic slides, borosilicate glass slides (1"×3"×1.1 mm) are plasma-cleaned overnight then coated with several layers of metals using magnetron sputtering. At least 6 layers are coated on each plasmonic slide. For layer 1, the first adherence layer, about 35-45 nm, preferably 40 nm of titanium dioxide ($TiO_2$), is deposited at about 2-5 angstroms per second, preferably at about 3 angstroms per second. For layer 2, a silver mirror layer, around 180-220 nm, preferably 200 nm of silver (Ag), is deposited at about 3-6 angstroms per second, preferably 4 angstroms per second. For layer 3, a second adherence layer, about 5-7 nm, preferably about 6 nm of titanium dioxide ($TiO_2$), is deposited at about 0.5-1.5 angstroms per second, preferably at about 1.0 angstrom per second. For layer 4, a dielectric layer, about 35-45 nm, preferably 40 nm of silicone dioxide ($SiO_2$), is deposited at about 0.5-1.5 angstroms per second, preferably 1.0 angstrom per second. For layer 5, a second silver layer, about 11-15 nm, preferably about 13 nm of silver (Ag), is deposited at about 0.1-1 angstroms per second, preferably about 0.5 angstroms per second. For layer 6, a stability layer, about 18-22 nm, preferably 20 nm of silicone dioxide ($SiO_2$), is deposited at around 0.5-1.5 angstroms per second, preferably 1.0 angstrom per second.

The slides are then vacuum-annealed at around 200° C. for 1 hour and are dried under nitrogen and sealed in an air-tight container until use. The slides are then ready for surface chemistry such as epoxy silane that will allow strong adherence of proteins, polynucleotides, or glycans. In some embodiments, epoxy-silane was applied on top of the $SiO_2$ layer using conventional dip methods, and slides were stored at −20° C. for up to 2 months prior to use.

For example, the multi-layer slides are placed in a solution of 50% (3-glycidyloxypropol) trimethoxysilane in 1,2 dichloroethane for 2.5 hours at room temperature, then thoroughly rinsed in 1,2 dichloroethane and dried under a stream of nitrogen. Coated slides are packaged in air-tight packaging and stored at room temperature until used.

Additionally, to compare with the plasmonic slides, conventional epoxy coated slides are also prepared (Corning Inc.). Biotinylated BSA is obtained from Pierce. The antibodies are obtained from Jackson ImmunoResearch Inc. The glycans are developed in-house in Z Biotech, LLC and the Glycan Binding Proteins are obtained from Vector Laboratories, Inc. The SA-Cy3 and SA-Cy5 are obtained from Thermo Fisher Scientific Inc. After obtaining all materials, slides are printed by diluting proteins or glycans in Z Biotech's printing buffer. All slides are printed on a proprietary printer at approximately 300 pL per spot. Resulting spots are approximately 200 μm in diameter. After a 1 hour incubation at room temperature, spotted slides are blocked with 1% BSA in 10 mM Tris-HCl pH 7.4.

Example 2

Spectroscopic Measurements

The method to measure fluorescent signals are well documented in the art. In one example, extinction spectra are measured with a Hewlett-Packard 8453 spectrophotometer relative to the bare glass. Reflectance spectra are acquired with a Varian Cary 100 Bio spectrophotometer equipped with an external specular reflection attachment with fixed angle of incidence of 12 degrees. For baseline correction, a reference aluminum mirror (reflectance accessory) is used. Scanning electron microscopy (Hitachi SU-70) is used for surface morphology imaging. Fluorescence from surfaces is measured using an epifluorescene microscope (Axiovert 135TV, Zeiss) with 10×, NA 0.30 objective (UPlanFI, Olympus). Excitation us provided using either a blue LED (Nichia NSPB500S) with peak wavelength at 470 nm or a red LED (Nichia N SPR510CS) at 630 nm, and the emission is never through a band-pass filter of 535/50 nm (AF488-SA) and long pass filter above 644 nm (red dyes). Fluorescent enhancement is determined as the intensity ratio of the fluorescent signal measured from the multilayer substrate over the signal from the respective reference sample on bare glass using identical experimental conditions. Time-resolved data are measured using a phase-modulation fluorometer (K2 from ISS, Champagne, Ill.). The LEDs are modulated by applying an RF driving signal from a Marconi model 2022A frequency synthesizer (from Marconi Instruments, Allendale, N.J.) to the LED.

Example 3

Protein Assay

Both plasmonic and conventional slides are printed as 16 identical 9×8 arrays. Each 9×8 array comprises the following components. The first 3 spots across the top of the array are biotinylated-BSA at a concentration of 0.1 mg/mL. The first 3 spots of each subsequent row are orders of magnitude dilutions of this, down to 0.1 ng/mL in the $8^{th}$ row. The first 3 spots in the $9^{th}$ row are a negative control (printing buffer). Additionally, the middle 3 spots of each row are mouse IgG starting at 0.1 mg/mL in the top row, going down to 0.1 ng/mL in the $8^{th}$ row. The middle 3 spots of the $9^{th}$ row are a positive control (anti-goat IgG labeled with Cy3 at 0.01 mg/mL). The last 3 spots of each row are human IgG starting at 0.1 mg/mL in the top row, going down to 0.1 ng/mL in the 8th row. The last 3 spots in the 9th row are blank.

Each of these arrays is probed with one of the following detection agents: Cy3 labeled streptavidin at 1 µg/mL, biotinylated anti-mouse IgG antibody at 1 µg/mL or biotinylated anti-human IgG antibody at 1 µg/mL. The last two are then re-probed with streptaviding-Cy3 at 0.5 µg/mL.

Example 4

Glycan Assay

Figure 2:
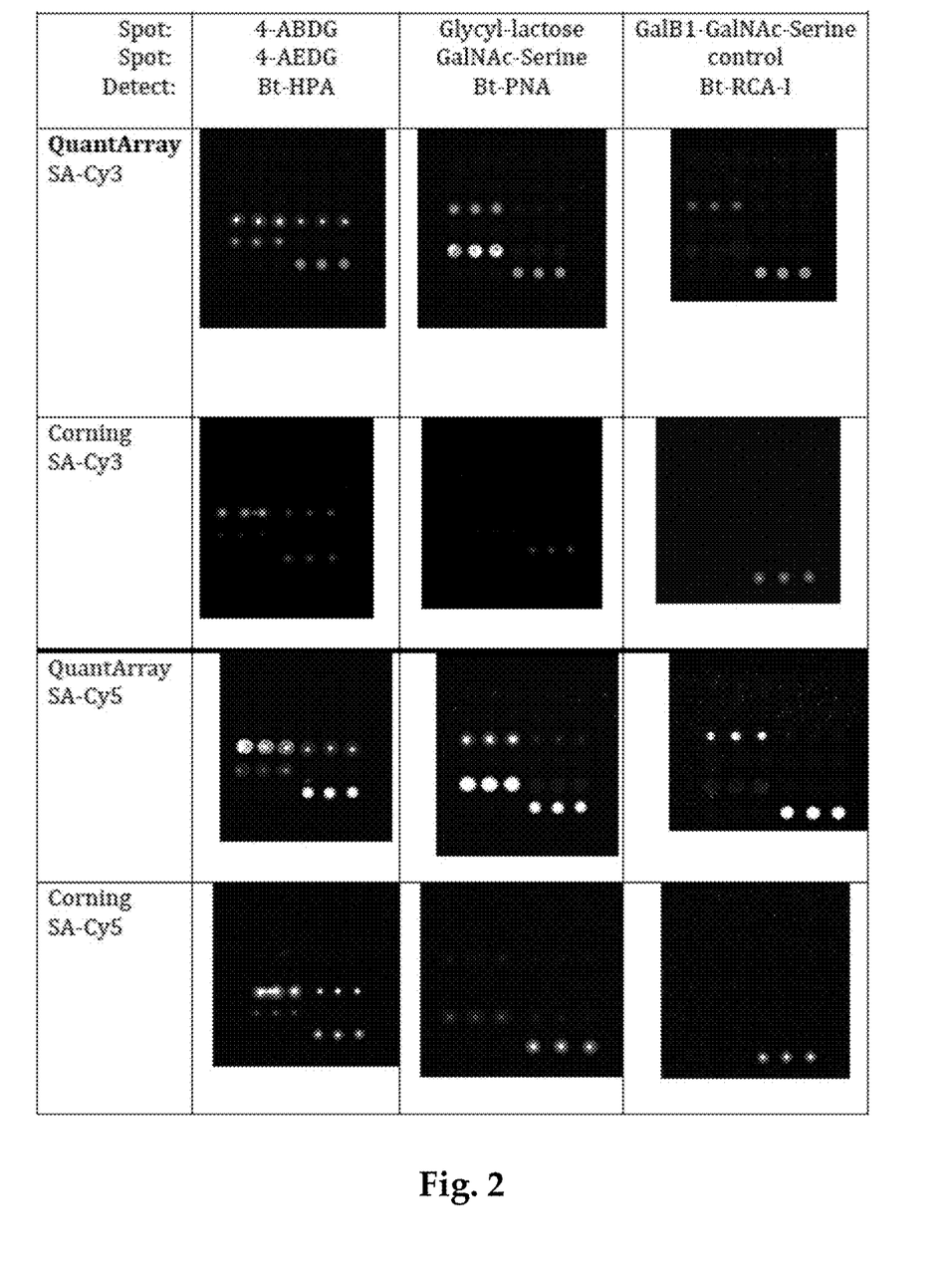

Both plasmonic and conventional slides are printed as 16 identical 6×6 arrays. Each 6×6 array comprises the following components. The first 3 spots of row 1 contain 4-aminobutyl β-D-galactopyranoside at 100 µM followed by 3 spots of this glycan at 10 µM. The first 3 spots in row 2 contain aminoethyl β-D-galactopyranoside at 100 µM, followed by 3 spots of this glycan at 10 µM. In row 3, the first 3 spots contain 100 µM of glycyl-lactose, followed by 3 spots of glycyl-lactose at 10 µM. In row 4, the first 3 spots contain 100 µM of α-GalNAc-Serine (Tn antigen) followed by 3 spots of 10 µM of this. In row 5, the first 3 spots contain Galβ1-3GalNAcα1-serine (T antigen) at 100 µM, followed by 3 spots of this at 10 µM. The first 3 spots in row 6 are a negative control followed by 3 spots of a positive control. Each of these arrays is assayed using either biotinylated-HPA at 10 µg/mL, PNA-biotin at 10 µg/mL or RCA-1-Biotin at 1 µg/mL followed by SA-Cy3 or SA-Cy5 at 0.5 ug/mL as indicated in FIG. 2.

Proteins, polynucleotides, and/or glycans printed on the slides can be further detected with a microarray scanner. Slides are read on an Axon4000 slide reader with GenePix Pro software at 532 nm for Cy3 and at 635 nm for Cy5.

Example 4

Fluorescence Enhancement Assay

To demonstrate that QuantArray-S-ES slides enhance fluorescence, the following assay was performed both on a QuantArray-S-ES slide and on a control glass slide that was epoxy silane coated at the same time as the QuantArray slides. Slides were spotted with various concentrations of biotinylated-BSA in 50 mM sodium phosphate buffer pH 7.0 containing 5% glycerol using a hand-spotting device from V&P Scientific that spots 6 nL spots. After a 30 min incubation at room temperature, the slides were blocked in 1% BSA and 1 mM EDTA in 10 mM Tris-HCl pH 7.6 for 60 min. After washing, slides were incubated in 1 ug/mL of streptavidin conjugated DyLight 633 (DL633) for 60 min at room temperature (RT), then washed and dried. Slides were scanned in a GenePi 4000 (Axon Instruments) scanner. It was found that QuantArray slides easily detected a spot of 0.006 pg of Bt-BSA, whereas the control slides barely detected a spot of 0.06 pg of Bt-BSA, demonstrating an approximately 30-fold enhancement of the signal.

REFERENCES

1. C. D. Geddes and J. R. Lakowicz, Metal-enhanced fluorescence, *J. Fluoresc.*, (2002), 12: 121-129.
2. Metal-Enhanced Fluorescence, ed. C. D. Geddes, John Wiley and Sons, New Jersey, 2010, pp. 625, ISBN: 9780-470-2238-8.
3. Aslan, K., Gryczynski, I., Malicka, J., Matveeva, E., Lakowicz, J. R. and Geddes, C. D. (2005). Metal-enhanced fluorescence: an emerging tool in biotechnology, *Current Opinion in Biotechnology*, 16: 55-62.
4. Plasmon-controlled fluorescence towards high-sensitivity optical sensing. Ray K, Howdhury M H, Zhang J, Fu Y, Szmacinski H, Nowaczyk, K, Lakowicz J R. Adv Biochem Eng Biotechnol (2009) 116: 29-72.
5. Advances in surface-enhanced fluoresence. Lakowicz J. R., Geddes C. D., Gryczynski I., Malicka J., Gryczynski Z., Aslan K., Lukomska J., Matveeva E., Zhang J., Badugu R., Huang J. (2004) *J Fluoresc* 14(4): 425-41.

What is claimed:

1. A multi-layer plasmonic slide comprising at least six layers in the order of:
   (a) a layer 1 comprising an adherence layer, wherein said adherence layer comprises titanium dioxide (dioxide (TiO2) and is between 35-45 nm);
   (b) a layer 2 comprising a silver mirror layer;
   (c) a layer 3 comprising an adherence layer;
   (d) a layer 4 comprising a dielectric layer;
   (e) a layer 5 comprising a thin silver layer; and
   (f) a layer 6 comprising a stabilization layer.
2. The multi-layer plasmonic slide of claim 1, wherein:
   (a) layer 1 comprises titanium dioxide (TiO2);
   (b) layer 2 comprises silver (Ag);
   (c) layer 3 comprises titanium dioxide (TiO2);
   (d) layer 4 comprises silicon dioxide (SiO2);
   (e) layer 5 comprises silver (Ag); and
   (f) layer 6 comprises silicon dioxide (SiO2).
3. The multi-layer plasmonic slide of claim 1, wherein layer 1 is:
   (a) about 40 nm;
   (b) deposited at about 2-5 angstroms per second; or
   (c) deposited at about 3 angstroms per second.
4. The multi-layer plasmonic slide of claim 1, wherein layer 2 is:
   (a) about 180-220 nm;
   (b) about 200 nm;
   (c) deposited at about 3-6 angstroms per second;
   (d) deposited at about 4 angstroms per second.
5. The multi-layer plasmonic slide of claim 1, wherein layer 3 is:
   (a) about 5-7 nm;
   (b) about 6 nm;
   (c) deposited at about 0.5-1.5 angstroms per second; or
   (d) deposited at about 1.0 angstrom per second.
6. The multi-layer plasmonic slide of claim 1, wherein layer 4 is:
   (a) about 35-45 nm;
   (b) about 40 nm;
   (c) deposited at about 0.5-1.5 angstroms per second; or
   (d) deposited at about 1.0 angstrom per second.
7. The multi-layer plasmonic slide of claim 1, wherein layer 5 is:
   (a) about 11-15 nm;
   (b) is about 13 nm;
   (c) deposited at about 0.1-1 angstroms per second;
   (d) deposited at about 0.5 angstrom per second.
8. The multi-layer plasmonic slide of claim 1, wherein layer 6 is:
   (a) about 18-22 nm;
   (b) about 20 nm;
   (c) deposited at about 0.5-1.5 angstroms per second; or
   (d) deposited at about 1.0 angstrom per second.

9. The multi-layer plasmonic slide of claim 1, wherein:
(a) layer 1 comprises about 40 nm of titanium dioxide (TiO2);
(b) layer 2 comprises about 200 nm of silver (Ag);
(c) layer 3 comprises about 6 nm of titanium dioxide (TiO2);
(d) layer 4 comprises about 40 nm of silicon dioxide (SiO2);
(e) layer 5 comprises about 13 nm of silver (Ag); and
(f) layer 6 comprises about 20 nm of silicon dioxide (SiO2).

10. The multi-layer plasmonic slide of claim 1, wherein:
(a) layer 1 comprises about 40 nm of titanium dioxide (TiO2) deposited at about 3 angstroms per second;
(b) layer 2 comprises about 200 nm of silver (Ag) deposited at about 4 angstroms per second;
(c) layer 3 comprises about 6 nm of titanium dioxide (TiO2) deposited at about 1 angstrom per second;
(d) layer 4 comprises about 40 nm of silicon dioxide (SiO2) deposited at 1 angstrom per second;
(e) layer 5 comprises about 13 nm of silver (Ag) deposited at about 0.5 angstroms per second; and
(f) layer 6 comprises about 20 nm of silicon dioxide (SiO2) deposited at about 1 angstrom per second.

11. The multi-layer plasmonic slide of claim 1, wherein the slide is:
(a) plasma-cleaned and the coating of each layer of the slide is accomplished by using magnetron sputtering;
(b) vacuum-annealed at about 150° C. to about 250° C.;
(c) vacuum-annealed at about 200° C.;
(d) further coated with epoxy silane;
(e) printed as a microarray in any size;
(f) printed at about 250-350 pL per spot and the resulting spot is about 150-250 μm in diameter; or
(g) printed at about 300 pL per spot and the resulting spot is about 200 μm in diameter.

12. The multi-layer plasmonic slide of claim 11, wherein the microarray is printed with a protein, a glycan, or an antibody.

13. The multi-layer plasmonic slide of claim 12, wherein the protein, the glycan, or the antibody is included in at least three spots on the microarray.

14. A method of detecting a concentration of a protein, a glycan, or an antibody, comprising:
(a) contacting a protein, a glycan, or an antibody with the multi-layer plasmonic slide of claim 1; and
(b) tagging a Cy5 fluorescent probe or a Cy3 fluorescent probe on a protein, a glycan, or an antibody; and
(c) detecting a protein, a glycan, or an antibody with a microarray laser scanner; and
(d) measuring the intensity of fluorescent signals at about 532 nm for Cy3 and at 635 nm for Cy5.

15. The method of claim 14, wherein the protein is biotinylated, or detected with an antibody.

16. The method of claim 14, wherein the concentration of the protein printed on the array is between 0.1 ng/ml and 0.1 mg/ml.

17. The method of claim 15, wherein:
(a) the antibody is a human IgG and is detected with biotinylated anti-human IgG followed by streptavidin-Cy3 or streptavidin-Cy5;
(b) the antibody is a mouse IgG and is detected with biotinylated anti-mouse IgG followed by streptavidin-Cy3 or streptavidin-Cy5;
(c) the biotinylated protein is BSA and the biotinylated-BSA is detected with either streptavidin-Cy3 or streptavidin-Cy5;
(d) the biotinylated protein is BSA and the biotinylated-BSA can be detected at least 1-2, 2-3, 3-4, or 4-5 orders of magnitude lower concentrations using Cy5 fluorescent probe;
(e) the biotinylated protein is BSA and the biotinylated-BSA is saturated at concentration of 0.01, 0.02, 0.03, 0.04, 0.05, 0.06, 0.07, 0.08, 0.09, or 0.1 mg/mL with streptavidin-Cy3; and/or
(f) the glycan is detected with a biotinylated-glycan binding protein followed by streptavidin-Cy3 or streptavidin-Cy5.

18. The method of claim 17, wherein at least 5 different glycans are detected.

19. The method of claim 18, wherein the glycans are selected from 4-aminobutyl β-D-galactopyranoside, aminoethyl β-D-galactopyranoside, glycyl-lactose, α-GalNAc-Serine, and Galβ1-3GalNAcα1-serine (T antigen).

20. The method of claim 17, wherein the glycans can be detected at least 2, 3, 4 or 5 orders of magnitude lower concentrations using Cy5 fluorescent probe.

21. The method of claim 14, wherein the detection with Cy5 fluorescent probe yields brighter spots on the microarray than Cy3 fluorescent probe.

22. A method of making the multi-layer plasmonic slide of claim 1, comprising:
(a) preparing a plasma-clean borosilicate glass slide; and
(b) Coating layer 1 of the slide with titanium dioxide (TiO2) by magnetron sputtering; and
(c) coating layer 2 of the slide with silver (Ag) by magnetron sputtering; and
(d) coating layer 3 of the slide with titanium dioxide (TiO2); and
(e) coating layer 4 of the slide with silicon dioxide (SiO2); and
(f) coating layer 5 of the slide with silver (Ag); and
(g) coating layer 6 of the slide with silicon dioxide (SiO2); and
(h) coating the slide with epoxy silane using a dipping process; and
(i) drying the slide under nitrogen and vacuum-annealing at about 200° C.

23. The method of claim 14, wherein the amount of the protein printed on the array is from 0.006 pg to 6 pg.

24. The method of claim 23, wherein the protein is biotinylated-BSA.

25. The method of claim 23, wherein the multi-layer plasmonic slide enhances fluorescent signals as compared to a control slide, and preferably about 30-fold as compared to the control slide.

26. The method of claim 15, wherein said antibody is a mouse IgG or a human IgG.

* * * * *